US011390595B2

(12) United States Patent
Ebertz

(10) Patent No.: US 11,390,595 B2
(45) Date of Patent: Jul. 19, 2022

(54) PROCESS FOR THE PREPARATION OF AN ACESULFAME WITH SULPHURIC ACID PROCESSING

(71) Applicant: CHEMADVICE GMBH, Wiesbaden (DE)

(72) Inventor: Hans Wolfgang Ebertz, Troisdorf (DE)

(73) Assignee: CHEMADVICE GMBH, Wiesbaden (DE)

( * ) Notice: Subject to any disclaimer, the term of this patent is extended or adjusted under 35 U.S.C. 154(b) by 7 days.

(21) Appl. No.: 16/963,145

(22) PCT Filed: Jan. 18, 2018

(86) PCT No.: PCT/EP2018/051243
§ 371 (c)(1),
(2) Date: Jul. 17, 2020

(87) PCT Pub. No.: WO2019/141369
PCT Pub. Date: Jul. 25, 2019

(65) Prior Publication Data
US 2021/0122720 A1  Apr. 29, 2021

(51) Int. Cl.
*C07D 291/06* (2006.01)
*B01J 14/00* (2006.01)

(52) U.S. Cl.
CPC ................... *C07D 291/06* (2013.01)

(58) Field of Classification Search
CPC ................ C07D 291/06; B01J 14/00
See application file for complete search history.

(56) References Cited

U.S. PATENT DOCUMENTS

| 4,876,341 A | 10/1989 | Schutz et al. |
| 7,829,701 B2 | 11/2010 | Liu et al. |
| 2009/0318685 A1 | 12/2009 | Saito et al. |

FOREIGN PATENT DOCUMENTS

| CN | 204320227 U | 5/2015 |
| CN | 103 613 566 B | 3/2016 |
| DE | 2453063 A1 | 5/1976 |
| EP | 1 564 211 A1 | 8/2005 |
| EP | 2 377 813 B1 | 12/2014 |
| EP | 2 560 919 B1 | 10/2015 |
| EP | 2 861 569 B1 | 2/2017 |
| WO | 93/19055 B1 | 9/1993 |
| WO | 2011133468 A1 | 10/2011 |

OTHER PUBLICATIONS

International Search Report for International Application No. PCT/EP2018/051243 dated Mar. 19, 2018.
Written Opinion for International Application No. PCT/EP2018/051243 dated Mar. 19, 2018.
Clauss, Karl et al., "Oxathiazinone Dioxides—A New Group of Sweetening Agents," Angewandte Chemie, Int. Ed. in English, 1973, 12(11), 869-876.

*Primary Examiner* — Laura L Stockton
(74) *Attorney, Agent, or Firm* — Meunier Carlin & Curfman LLC

(57) ABSTRACT

The present invention generally relates to a process for the preparation of a product, the product being 6-methyl-3,4-dihydro1,2,3-oxathiazin-4-one 2,2-dioxide or a derivative thereof. The present invention also relates to the use of such a process for making diammonium sulphate. The present invention relates to a process for the preparation of a product, the product being 6-methyl-3,4-dihydro1,2,3-oxathiazin-4-one 2,2-dioxide or a derivative thereof, the process comprising the following steps:

a. Contacting $SO_3$ and acetoacetamide-N-sulphonic acid or a derivative thereof in the presence of an amine, thereby obtaining a first stream comprising the amine and sulphuric acid;
b. Providing a second stream comprising ammonia;
c. Providing a circuit;
d. Introducing the second stream into the circuit at point A and the first stream into the circuit at point B to obtain a cycle stream cycling in the circuit;
e. Removing a portion of the cycle stream at a point C to obtain a third stream;

wherein the circulation ratio is in the range from 3 to 30, the circulation ratio being the value of the mass flow rate of the cycle stream immediately preceding point A $F_c$ divided by the value of the mass flow rate of the first stream into the circuit at point B $F_1$ according to the following formula:

circulation ratio=$F_c/F_1$.

15 Claims, 4 Drawing Sheets

PROCESS FOR THE PREPARATION OF AN ACESULFAME WITH SULPHURIC ACID PROCESSING

CROSS REFERENCE TO RELATED APPLICATION

This is a national stage application of PCT/EP2018/051243 filed Jan. 18, 2018, the contents of which is incorporated herein by reference.

FIELD OF THE INVENTION

The present invention generally relates to a process for the preparation of a product, the product being 6-methyl-3,4-dihydro1,2,3-oxathiazin-4-one 2,2-dioxide or a derivative thereof. The present invention also relates to the use of such a process for making diammonium sulphate.

BACKGROUND

Acesulfame and its derivatives are hugely important as sweeteners in food stuffs and in medicines. Of particular interest are the non-toxic salts, of which the potassium salt acesulfame K is most noteworthy. Acesulfame K is often marketed under the tradenames Sunett® and Sweet One® and is designated with the E number E950 in the European Union. In view of the huge demand for acesulfame as a sweetener, around twenty thousand metric tonnes per annum globally, there is a great need for improved processes for its production and even minor improvements to the production processes can result in huge savings, both economically and ecologically.

Early approaches to acesulfame production employed halogen based intermediates. A number of examples are presented in Angewandte Chemie 85, No. 22 (1973), pages 965 to 73, corresponding to International Edition Vol. 12, No. 11 (1973), pages 869-76. There, the processes overwhelmingly start from chlorosulphonyl or fluorosulphonyl isocyanate. Another example is given in German patent publication number 2,453,063 where a process starting from amidosulphonyl fluoride is disclosed.

A process for the preparation of acesulfame which proceeds via an acetoacetamide-N-sulphonic acid can offer the advantage of starting from more readily accessible starting materials. One example of such a process is presented in Chinese patent application 201310531442.

European patent document EP 2 560 919 B2 describes a process for preparing diammonium sulphate.

There remains however a need for improved processes for the preparation of acesulfame, in particular with sulphuric acid removal.

SUMMARY OF THE INVENTION

Generally, it is an object of the present invention to at least partly overcome a disadvantage arising from the prior art.

It is an object of the invention to provide a process for the preparation of acesulfame or a derivative thereof with a reduced energy consumption.

It is an object of the invention to provide a process for the preparation of acesulfame or a derivative thereof in which the conversion of spent sulphuric acid into diammonium sulphate has a reduced energy consumption.

It is an object of the invention to provide a process for the preparation of acesulfame or a derivative thereof with a reduced energy consumption in two or more process steps.

It is an object of the invention to provide a process for the preparation of acesulfame or a derivative thereof which has a reduced environmental impact.

DETAILED DESCRIPTION

Throughout this document, a hydrolysis step is also referred to as a step of contacting with $H_2O$.

6-methyl-3,4-dihydro1,2,3-oxathiazin-4-one 2,2-dioxide is also called acesulfame and the term acesulfame is used throughout this document as a synonym of 6-methyl-3,4-dihydro1,2,3-oxathiazin-4-one 2,2-dioxide.

A contribution to achieving at least one of the above objects is made by the claims. A contribution to achieving at least one of the above objects is made by the following embodiments, the number of the embodiment being indicated between vertical bars.

|1| A process for the preparation of a product, the product being 6-methyl-3,4-dihydro1,2,3-oxathiazin-4-one 2,2-dioxide or a derivative thereof, the process comprising the following steps:
 a. Contacting $SO_3$ and acetoacetamide-N-sulphonic acid or a derivative thereof in the presence of an amine, thereby obtaining a first stream comprising the amine and sulphuric acid;
 b. Providing a second stream comprising ammonia;
 c. Providing a circuit;
 d. Introducing the second stream into the circuit at point A and the first stream into the circuit at point B to obtain a cycle stream cycling in the circuit;
 e. Removing a portion of the cycle stream at a point C to obtain a third stream;
wherein the circulation ratio is in the range from 3 to 30, preferably in the range from 4 to 20, more preferably in the range from 5 to 15, more preferably in the range from 6 to 12, more preferably in the range from 8 to 11, the circulation ratio being the value of the mass flow rate of the cycle stream immediately preceding point A $F_c$ divided by the value of the mass flow rate of the first stream into the circuit at point B $F_1$ according to the following formula:

$$\text{circulation ratio} = F_c/F_1$$

In one aspect of this embodiment, the first stream satisfies one or more of the following criteria:
 i.) The content of sulphuric acid is in the range from 35 to 75 wt. %, preferably in the range from 45 to 65 wt. %, most preferably in the range from 50 to 60 wt. %;
 ii.) The content of the amine is in the range from 5 to 25 wt. %, preferably in the range from 8 to 20 wt. %, most preferably in the range from 10 to 15 wt. %.
 iii.) The content of $H_2O$ is in the range from 10 to 60 wt. %, preferably in the range from 20 to 50 wt. %, most preferably in the range from 25 to 40 wt. %.
 iv.) The first stream does not contain more than 1 wt. % dichloromethane, preferably not more than 0.5 wt. %, more preferably not more than 0.1 wt. %, more preferably not more than 0.05 wt. %.

In one aspect of this embodiment, the second stream satisfies one or more of the following criteria:
 i.) The content of ammonia is in the range from 90 to 100 wt. %, preferably in the range from 95 to 100 wt. %, most preferably in the range from 99 to 100 wt. %;
 ii.) The content of $H_2O$ is in the range from 0 to 10 wt. %, preferably in the range from 0 to 5 wt. %, most preferably in the range from 0 to 1 wt. %.

In one aspect of this embodiment, the third stream satisfies one or more of the following criteria:

i.) The content of $H_2O$ is in the range from 10 to 45 wt. %, preferably in the range from 15 to 35 wt. %, most preferably in the range from 20 to 30 wt. %;

ii.) The content of diammonium sulphate is in the range from 20 to 85 wt. %, preferably in the range from 25 to 75 wt. %, most preferably in the range from 40 to 70 wt. %;

iii.) The content of the amine is in the range from 5 to 30 wt. %, preferably in the range from 10 to 25 wt. %, most preferably in the range from 8 to 20 wt. %.

|2| The process according to embodiment |1|, wherein the amine is triethyl amine.

|3| The process according to embodiment |1| or |2|, wherein the third stream is removed from the cycle stream at a point C and the points A, B & C are ordered in the direction of the flow of the cycle stream in the circuit.

|4| The process according to any of the preceding embodiments, wherein the second stream does not comprise more than 50 wt. % $H_2O$, preferably not more than 40 wt. %, more preferably not more than 30 wt. %, more preferably not more than 20 wt. %, more preferably not more than 10 wt. %, more preferably not more than 5 wt. %, more preferably not more than 2 wt. %, more preferably not more than 1 wt. %. Most preferably the second stream is free of $H_2O$.

|5| The process according to any of the preceding embodiments, wherein the second stream is a liquid.

|6| The process according to any of the preceding embodiments, wherein the second stream is at a pressure in the range from 0.2 to 1.5 MPa, preferably in the range from 0.25 to 1.4 MPa, more preferably in the range from 0.3 to 1.3 MPa.

|7| The process according to any of the preceding embodiments, further comprising the following step:
f. Separating the third stream to obtain a fourth stream comprising the amine and a fifth stream comprising diammonium sulphate;

wherein the fourth stream comprises a higher wt. % of the amine than the first stream;

wherein the fourth stream comprises a lower wt. % of diammonium sulphate than the first stream.

The separation step f. is preferably a phase separation, preferably into a volatile phase and a liquid. The fourth stream is preferably a volatile phase. The fifth stream is preferably a liquid. A preferred volatile phase is a gas. Preferably, the volatile phase is an azeotrope.

In one aspect of this embodiment, the fourth stream satisfies the following criterion:
i.) The content of the amine is in the range from 60 to 95 wt. %, preferably in the range from 65 to 90 wt. %, more preferably in the range from 70 to 80 wt. %.

In one aspect of this embodiment, the fifth stream satisfies the following criterion:
i.) The content of diammonium sulphate is in the range from 30 to 85 wt. %, preferably in the range from 35 to 80 wt. %, more preferably in the range from 45 to 75 wt. %.

|8| The process according to embodiment |7|, wherein the fifth stream is contacted with $H_2O$ in a step $g_1$.

|9| The process according to embodiment |8|, wherein least part of the $H_2O$ is present in step $g_1$ in a gaseous state, preferably all the $H_2O$.

|10| The process according to any of the embodiments |7| to |9|, wherein the mass ratio of the fourth stream to the fifth stream is in the range from 30:70 to 1:99, more preferably in the range from 20:80 to 2:98, more preferably in the range from 15:85 to 5:95.

|11| The process according to any of the embodiments |7| to |10|, wherein the content of $H_2O$ in the fifth stream is reduced in a step $g_2$. In one aspect of this embodiment, some $H_2O$ remains in the fifth stream following step $g_2$. In another aspect of this embodiment, the content of $H_2O$ in the fifth stream is reduced to substantially none.

|12| The process according to embodiment |11|, wherein the step $g_2$ is a solidification. Preferred solidifications are one or more selected from the group consisting of: a crystallisation, a precipitation and a drying.

|13| The process according to any of the embodiments |7| to |12|, wherein the fourth stream is separated into a sixth stream and a seventh stream in a step h;

wherein the seventh stream comprises more $H_2O$ than the sixth stream;

wherein the sixth stream comprises more of the amine than the seventh stream.

|14| The process according to embodiment |13|, wherein the step h is a distillation.

|15| The process according to any of the preceding embodiments, wherein the cycle stream is heated or cooled, preferably by a heat exchanger. The heat exchanger is preferably an active heat exchanger. Heat extracted from the cycle stream may be used for stripping sulphuric acid fed into the reaction as the first stream.

|16| A use of the process according to any of the preceding embodiments for making diammonium sulphate.

Process

A contribution to achieving at least one of the above mentioned objects is made by a process for the preparation of a product, the product being 6-methyl-3,4-dihydro1,2,3-oxathiazin-4-one 2,2-dioxide or a derivative thereof, the process comprising the following steps:

a. Contacting $SO_3$ and acetoacetamide-N-sulphonic acid or a derivative thereof in the presence of an amine, thereby obtaining a first stream comprising the amine and sulphuric acid;

b. Providing a second stream comprising ammonia;

c. Providing a circuit;

d. Introducing the second stream into the circuit at point A and the first stream into the circuit at point B to obtain a cycle stream cycling in the circuit;

e. Removing a portion of the cycle stream at a point C to obtain a third stream;

Contacting Step a. & Acesulfame Production

Contacting Step a. Preferably Produces an Acesulfame.

In one embodiment, the contacting step a. may constitute a series of chemical reactions such as that presented in the following chemical equation I:

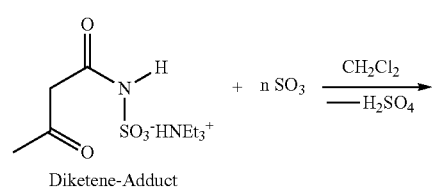

Diketene-Adduct

I

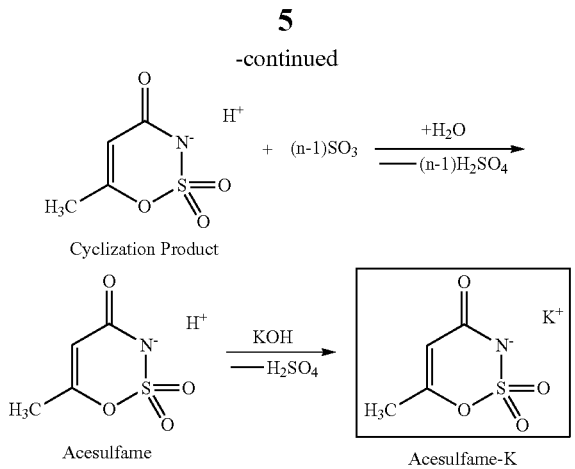

In other embodiments, the process may comprise a series of chemical reactions similar to those presented in chemical equation I. In one aspect of this embodiment, a solvent other than $CH_2Cl_2$ is employed, preferably one selected from the solvents section below. In one aspect of this embodiment, a base different to KOH is employed and the resulting acesulfame has a correspondingly different cation. In one aspect of this embodiment, an amine different to triethyl amine is employed. In one aspect of this embodiment, an equimolar amount of $SO_3$ is employed, namely the parameter n is set to 1. Here, the formula (n−1) is equal to zero and no $H_2O$ is employed.

The process of the invention preferably includes a ring closure reaction in which the acetoacetamide-N-sulphonic acid or derivative thereof reacts to form a ring. The ring closure is preferably assisted by the $SO_3$.

In one embodiment of the process, a sub-step of contacting with $H_2O$ is performed as part of step a. A sub-step of contacting with $H_2O$ is preferably employed for hydrolysing an adduct, preferably an adduct comprising $SO_3$.

In one embodiment, a sub-step of neutralising with alkali is performed as part of step a. and preferably following the sub-step of contacting with $H_2O$ were one is performed.

In one preferred embodiment, the contacting step a. may be carried out at least partially in a reactor, preferably a tubular reactor. In one aspect of this embodiment, the contacting step a. may be performed at elevated pressure or elevated temperature or both. In one aspect of this embodiment, the first stream exits the reactor as a spray.

In one embodiment, the contacting step a. is performed at a temperature in the range from −70 to 175° C., preferably in the range from 40 to 150° C., more preferably in the range from 60 to 130° C., most preferably in the range from 80 to 120° C.

In one embodiment, the contacting step a. is performed at a pressure in the range from 0.2 to 2 MPa, preferably in the range from 0.3 to 1.5 MPa, more preferably in the range from 0.4 to 1.2 MPa, most preferably in the range from 0.5 to 1 MPa.

In one embodiment, the molar ratio in step a. of the $SO_3$ to the acetoacetamide-N-sulphonic acid or derivative thereof is in the range from 1:1 to 20:1, preferably in the range form 2:1 to 17:1, more preferably in the range from 2.5:1 to 15:1, most preferably in the range from 3:1 to 10:1.

The first stream is preferably derived from the product of the contacting in step a. by extracting acesulfame from sulphuric acid using a solvent, preferably with an extraction column. In one embodiment, acesulfame is extracted from sulphuric acid using dichloro methane (DCM). In one aspect of this embodiment, the DCM is at least partially removed to obtain the first stream.

In one embodiment, a step of contacting with a solvent is performed in contacting step a. and preferably subsequently to the step of contacting with water if one is performed. Preferred solvents in this context are inert solvents. An inert solvent preferably does not react chemically with the acetoacetamide-N-sulphonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$. Preferred solvents for the acetoacetamide-N-sulphonic acid or derivative thereof are one or more selected from the group consisting of the following: halogenated aliphatic hydrocarbons, aliphatic sulphoxides and aliphatic sulphones. Preferred halogenated aliphatic hydrocarbons have up to four carbon atoms, preferably one or more selected from the group consisting of the following: methylene chloride, chloroform and 1,2-dichloroethane. The preferred aliphatic sulphoxide is dimethyl sulphoxide. The preferred aliphatic sulphone is sulpholane. In one embodiment, the solvent for the acetoacetamide-N-sulphonic acid or derivative thereof is one or more selected form the group consisting of the following: methylene chloride and 1,2-dichloroethane, preferably methylene chloride.

In one embodiment, step a. comprises a sub-step of at least partially removing a solvent from the sulphuric acid, preferably dichloromethane. The content of the solvent in the sulphuric acid, preferably the dichloromethane, is preferably reduced by heating.

The amine of step a. can be a monoalkyl amine, a dialkyl amine or a trialkyl amine, preferably a trialkyl amine. Preferred trialkyl amines are trimethyl amine, triethyl amine and tripropyl amine, preferably triethyl amine. Preferred monoalkyl amines are monomethyl amine, monoethyl amine and monopropyl amine, preferably monoethyl amine. Preferred dialkyl amines are dimethyl amine, diethyl amine and dipropyl amine, preferably diethyl amine. The preferred amine is triethyl amine.

Hydrolysis

Step a. may comprise a hydrolysis sub-step. A hydrolysis sub-step is preferably a sub-step of contacting the product of the reaction of step a. with $H_2O$. Throughout this document, a hydrolysis sub-step may be termed as such or as a sub-step of contacting with $H_2O$. A hydrolysis sub-step is particularly preferred where the product of the reaction in step a. is an adduct, preferably an adduct with $SO_3$. Where a hydrolysis is performed, a separation sub-step is preferably also performed for removing a hydrolysis product, preferably for removing sulphuric acid.

The sub-step of contacting with $H_2O$ preferably produces a mixture comprising acesulfame or a derivative thereof, sulphuric acid and $H_2O$. The amount of $H_2O$ employed in the sub-step of contacting with $H_2O$ is preferably selected such that the resulting mixture comprises a weight ratio of sulphuric acid:$H_2O$ in the range from 1:10 to 10:1, preferably in the range from 1:3 to 5:1, more preferably in the range from 1:1 to 3:1. In one embodiment, the sub-step of contacting with $H_2O$ is performed as a continuous process. In this embodiment, the ratio of sulphuric acid to $H_2O$ is set by adapting a flow rate of $H_2O$.

In one embodiment, the $H_2O$ for the hydrolysis sub-step is in a vapour phase. In one embodiment, the $H_2O$ for the hydrolysis sub-step is in a liquid phase. In one embodiment, the $H_2O$ for the hydrolysis sub-step comprises a vapour phase and a liquid phase.

Reactor

The contacting step a. is preferably carried out in a reactor. The reactor is preferably configured and adapted to withstand elevated pressure and elevated temperature. In one embodiment, the reactor is configured and adapted to withstand the temperatures employed for the contacting step a. In another embodiment, the reactor is configured and adapted to withstand temperatures up to 140° C., preferably 175° C., more preferably up to 200° C. In one embodiment, the reactor is configured and adapted to withstand the pressures employed for the contacting step a. In another embodiment, the reactor is configured and adapted to withstand pressures up to 1.6 MPa, preferably up to 2.5 MPa, more preferably up to 3.2 MPa.

In one embodiment, the reactor is a tubular reactor, preferably a cylindrical tubular reactor. In one embodiment, the reactor comprises a tube, preferably a cylindrical tube. The interior of a tube or of a tubular reactor is also referred to as a bore. The tube is preferably adapted and configured to result in a pressure drop between the reactor and outside the reactor, preferably a pressure drop of more than 0.05 MPa. A preferred tube is adapted and configured to cause spraying of the product.

The reactor preferably contains a mixer, preferably a static mixer.

Contacting the First and the Second Stream

The first stream and the second stream are contacted in the circuit. The first stream comprises sulphuric acid and the second stream comprises ammonia. The contacting preferably produces diammonium sulphate. The first stream and the second stream are not contacted directly, rather each is introduced into the cycle stream, wherein they react.

Reaction between sulphuric acid and ammonia is exothermic. The reaction heat preferably serves to provide sufficient reaction temperature to the starting materials and for volatilising a fourth stream. A part or all of the third stream may be used as heating medium to strip the spent sulphuric acid before it enters the reaction as first stream. Thus, the heat of reaction reduces the energy consumption of the stripping step.

The cycle stream may be heated or cooled, in particular for adapting the rate of volatilisation from the third stream.

Step f.—Separation of the Third Stream

In the separation step f., the third stream is separated into a fourth stream and a fifth stream. The fourth stream preferably comprises $H_2O$ and the amine, preferably as an azeotrope. The fourth stream is preferably a volatile phase. A preferred volatile phase is a gas. Preferably, the volatile phase is an azeotrope. The fourth stream can subsequently be split in order to recover the amine. The fifth stream preferably comprises $H_2O$ and diammonium sulphate. The fifth stream is preferably a liquid. The fifth stream can subsequently be treated with $H_2O$, preferably steam. The fifth stream can subsequently have $H_2O$ removed, preferably to solidify diammonium sulphate.

The separation of the third stream into the fourth stream and the fifth stream is preferably a phase separation, preferably with the fourth stream being a volatile phase and the fifth stream being a liquid. A preferred volatile phase is a gas. Preferably, the volatile phase is an azeotrope.

The separation step f. is preferably performed in a separator, preferably a phase separator. Another term for a separator is a Splitter.

Step $g_1$—contacting of the fifth stream with $H_2O$

The fifth stream may be contacted with $H_2O$ in a step $g_1$, preferably to obtain an aqueous solution of diammonium sulphate. Contacting with $H_2O$ preferably reduces the content of the amine in the fifth stream. Amine removed from the fifth stream in step $g_1$ may be introduced into the fourth stream.

Step $g_2$—Reduction of $H_2O$ Content

The fifth stream may be treated to reduce its content of $H_2O$ in a step $g_2$. Step $g_2$ is preferably a solidification step. Reduction of content of $H_2O$, preferably solidification, is preferably effect by spray drying, preferably with heated gas, preferably air. Preferred solidifications are one or more selected from the following: a crystallisation, a precipitation and a drying. A crystallisation can be used to reduce the content of a material in the fifth stream other than diammonium sulphate or $H_2O$.

Step h—Separation of the Amine and $H_2O$

The fourth stream may be separated into a sixth stream and a seventh stream, wherein the seventh stream comprises more $H_2O$ than the sixth stream and wherein the sixth stream comprises more of the amine than the seventh stream. The separation of step h is preferably a phase separation and a distillation. The amine content of the sixth stream can be collected at the bottom of a distillation apparatus.

$SO_3$

A contribution to achieving at least one of the above mentioned objects is made by a process in which $SO_3$ is employed as a starting material. $SO_3$ is preferably employed in an amount by mols which is at least equal to the amount by mols of the acetoacetamide-N-sulphonic acid or a derivative thereof, preferably with the molar ratio in step a. of the $SO_3$ to the acetoacetamide-N-sulphonic acid or derivative thereof being in the range from 1:1 to 20:1, preferably in the range form 2:1 to 17:1, more preferably in the range from 2.5:1 to 15:1, most preferably in the range from 3:1 to 10:1. In one embodiment, $SO_3$ is employed in an approximately equimolar amount to the acetoacetamide-N-sulphonic acid or a derivative thereof. In this case, it can be that insufficient $SO_3$ is present for forming an adduct. In one aspect of this embodiment no step of contacting with $H_2O$ is required. In one embodiment, a molar excess of $SO_3$ is employed, preferably with the molar ratio in step a. of the $SO_3$ to the acetoacetamide-N-sulphonic acid or derivative thereof being in the range from greater than 1:1 to 20:1, preferably in the range form 2:1 to 17:1, more preferably in the range from 2.5:1 to 15:1, most preferably in the range from 3:1 to 10:1.

In one embodiment of the invention, $SO_3$ is provided in step a. in a first solvent.

In another embodiment, $SO_3$ is provided in step a. as a liquid.

Acetoacetamide-N-Sulphonic Acid or a Derivative Thereof

Acetoacetamide-N-sulphonic acid or a derivative thereof is employed in the process according to the invention. Acetoacetamide-N-sulphonic acid is also known by its chemical formula $CH_3COCH_2CONHSO_3H$ and the term Acetoacetamide-N-sulphonic acid and the formula $CH_3COCH_2CONHSO_3H$ shall be used interchangeably in this document.

Preferred derivatives of Acetoacetamide-N-sulphonic acid are salts, preferably having the formula $CH_3COCH_2CONHSO_3^-M^+$. A preferred $M^+$ is selected from the group consisting of $Na^+$, $K^+$, $Ca^+$, $Li^+$, ammonium and an aliphatic ammonium. Preferred aliphatic ammoniums in this context are one or more selected from the group consisting of: monoethyl ammonium, diethyl ammonium, triethyl ammonium, methyl ammonium, dimethyl ammonium and tri methyl ammonium. The preferred aliphatic ammonium is triethyl ammonium.

The Acetoacetamide-N-sulphonic acid or derivative thereof might be procured or formed in a process preceding step a. of the process of the invention. On preferred route for forming Acetoacetamide-N-sulphonic acid or a derivative thereof is by reacting amidosulphonic acid or a derivative thereof with an acetoacetylating agent, preferably in approximately equimolar amounts. Preferred derivatives of amidosulphonic acid in this contexts are salts, preferably with a cation selected form the group consisting of $Na^+$, $K^+$, $Ca^+$, $Li^+$, ammonium and an aliphatic ammonium. Preferred aliphatic ammoniums in this context are one or more selected from the group consisting of: monoethyl ammonium, diethyl ammonium, triethyl ammonium, methyl ammonium, dimethyl ammonium and tri methyl ammonium. The preferred aliphatic ammonium is triethyl ammonium.

The preferred acetoacetylating agent is diketene.

In one embodiment, the acetoacetamide-N-sulphonic acid or derivative thereof for the contacting step a. is provided in a second solvent.

Solvents

One or more solvents may be employed in the process of the invention, for example in one or more of the following roles: as a vehicle for the $SO_3$, as a vehicle for the acetoacetamide-N-sulphonic acid or derivative thereof, as a reaction medium in the reactor or for providing evaporative cooling.

Preferred solvents for the acetoacetamide-N-sulphonic acid or derivative thereof are inert solvents. An inert solvent preferably does not react chemically with the acetoacetamide-N-sulphonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$. Preferred solvents for the acetoacetamide-N-sulphonic acid or derivative thereof are one or more selected from the group consisting of the following: halogenated aliphatic hydrocarbons, aliphatic sulphoxides and aliphatic sulphones. Preferred halogenated aliphatic hydrocarbons have up to four carbon atoms, preferably one or more selected from the group consisting of the following: methylene chloride, chloroform and 1,2-dichloroethane. The preferred aliphatic sulphoxide is dimethyl sulphoxide. The preferred aliphatic sulphone is sulpholane. In one embodiment, the solvent for the acetoacetamide-N-sulphonic acid or derivative thereof is one or more selected form the group consisting of the following: methylene chloride and 1,2-dichloroethane, preferably methylene chloride.

Preferred solvents for the $SO_3$ are inert solvents. An inert solvent preferably does not react chemically with the acetoacetamide-N-sulphonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$. Preferred solvents for the $SO_3$ may be inorganic solvents or organic solvents or both. The preferred inorganic solvent is $SO_2$. Preferred organic solvents are one or more selected from the group consisting of the following: halogenated aliphatic hydrocarbons, aliphatic sulphones. Preferred halogenated aliphatic hydrocarbons have up to four carbon atoms, preferably one or more selected form the group consisting of the following: methylene chloride, chloroform and 1,2-dichloroethane. The preferred aliphatic sulphone is sulpholane. In one embodiment, the solvent is $SO_2$ or methylene chloride or both.

In a preferred embodiment of the process according to the invention the same solvent is used both for the acetoacetamide-N-sulphonic acid or derivative thereof and for the $SO_3$. Preferred solvents in this context are halogenated aliphatic hydrocarbons, most preferably methylene chloride.

In one embodiment, the contacting in step a. is performed in the presence of a reaction solvent. In one aspect of this embodiment, the reaction solvent is a chemical compound. In another aspect of this embodiment, the reaction solvent is two or more chemical compounds. In one aspect of this embodiment, the reaction solvent is an inert solvent. An inert solvent preferably does not react chemically with the acetoacetamide-N-sulphonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$. In one aspect of this embodiment, the reaction solvent comprises a halogenated hydrocarbon. In one aspect of this embodiment, the reaction solvent is a halogenated hydrocarbon. In one aspect of this embodiment, the reaction solvent comprises dichloromethane. In one aspect of this embodiment, the reaction solvent is dichloromethane.

In one embodiment, the $SO_3$ for the contacting step a. is provided in a first solvent. In one aspect of this embodiment, the first solvent is a chemical compound. In another aspect of this embodiment, the first solvent is two or more chemical compounds. In one aspect of this embodiment, the first solvent is an inert solvent. An inert solvent preferably does not react chemically with the acetoacetamide-N-sulphonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$. In one aspect of this embodiment, the first solvent comprises a halogenated hydrocarbon. In one aspect of this embodiment, the first solvent is a halogenated hydrocarbon. In one aspect of this embodiment, the first solvent comprises dichloromethane. In one aspect of this embodiment, the first solvent is dichloromethane. In one aspect of this embodiment, the concentration of $SO_3$ in the first solvent is in the range from 0.05 to 20 molar, preferably in the range from 0.1 to 15 molar, more preferably in the range from 0.15 to 10 molar, most preferably in the range from 0.2 to 6 molar.

In one embodiment, the acetoacetamide-N-sulphonic acid or a derivative thereof for the contacting step a. is provided in a second solvent. In one aspect of this embodiment, the second solvent is a chemical compound. In another aspect of this embodiment, the second solvent is two or more chemical compounds. In one aspect of this embodiment, the second solvent is an inert solvent. An inert solvent preferably does not react chemically with the acetoacetamide-N-sulphonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$. In one aspect of this embodiment, the second solvent comprises a halogenated hydrocarbon. In one aspect of this embodiment, the second solvent is a halogenated hydrocarbon. In one aspect of this embodiment, the second solvent comprises dichloromethane. In one aspect of this embodiment, the second solvent is dichloromethane. In one aspect of this embodiment, the concentration of the acetoacetamide-N-sulphonic acid or a derivative thereof in the second solvent is in the range from 0.02 to 5 molar, preferably in the range from 0.03 to 3 molar, more preferably in the range from 0.04 to 2 molar, most preferably in the range from 0.05 to 1.5 molar.

In one embodiment, the process according to any of the preceding embodiments, wherein the $SO_3$ for the contacting step a. is provided in a first solvent and the acetoacetamide-N-sulphonic acid or a derivative thereof for the contacting step a. is provided in a second solvent and the first solvent and the second solvent are the same. In one aspect of this embodiment, the first solvent is a chemical compound. In another aspect of this embodiment, the first solvent is two or more chemical compounds. In one aspect of this embodiment, the first solvent is an inert solvent. An inert solvent preferably does not react chemically with the acetoacetamide-N-sulphonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$. In one aspect of this embodiment, the first solvent comprises a halogenated hydrocarbon. In one aspect of this embodiment, the first solvent is a halogenated hydrocarbon. In one aspect of this embodiment, the first solvent comprises dichloromethane. In one aspect of this embodiment, the first solvent is dichloromethane.

Product

The process of the invention is preferably for the preparation of 6-methyl-3,4-dihydro1,2,3-oxathiazin-4-one 2,2-dioxide or a derivative thereof 6-methyl-3,4-dihydro1,2,3-oxathiazin-4-one 2,2-dioxide is also called acesulfame and the term acesulfame is used throughout this document as a synonym of 6-methyl-3,4-dihydro1,2,3-oxathiazin-4-one 2,2-dioxide.

The product of the present invention can be used as a food ingredient, preferably as a sweetener. Quite often, acesulfames are categorised as high intensity sweeteners. In one embodiment, the acesulfame or derivative thereof is non-toxic. In one embodiment, the acesulfame or derivative thereof can be hydrolysed, preferably at elevated temperature in acidic media, preferably resulting in non-toxic hydrolysis products.

Acesulfame is often prepared or usefully employed in the form of a salt. In one embodiment, the product is a salt of acesulfame. Preferred salts of acesulfame comprise the conjugate base of acesulfame and a cation. Preferred cations in this context are one or more selected from the group consisting of the following: $Na^+$, $K^+$, $Ca^+$ and aspartame, preferably K. In one embodiment, the preferred cation is selected form the group consisting of $Na^+$, $K^+$ and $Ca^+$, preferably $K^+$. In another embodiment, the cation is aspartame. The salt is preferably formed by removing the acidic hydrogen from the nitrogen atom of the acesulfame or derivative thereof. The product of the present invention can be used as a food ingredient. In one embodiment, the acesulfame salt is non-toxic. In one embodiment, the acesulfame salt can be hydrolysed, preferably at elevated temperature in acidic media, preferably resulting in non-toxic hydrolysis products.

Acesulfame can be prepared in the form of an adduct, either as an end product or as an intermediate. In one embodiment, the product is an adduct comprising acesulfame or a derivative thereof. Preferred adducts are formed with electron acceptors, also called Lewis acids. In one aspect of this embodiment, the preferred adduct is formed with $SO_3$. In one aspect of this embodiment, the product is an adduct of 6-methyl-3,4-dihydro1,2,3-oxathiazin-4-one 2,2-dioxide with $SO_3$ also called acesulfame:$SO_3$ adduct. The acesulfame:$SO_3$ adduct may comprise 1 or more $SO_3$ entities. In one aspect the acesulfame:$SO_3$ adduct may comprise 1, 2, 3, 4, 5, 6, 7 or 8 $SO_3$ entities. In one aspect the acesulfame:$SO_3$ adduct may comprise 1 to 8 $SO_3$ entities, preferably 1 to 7, more preferably 1 to 6, more preferably still 1 to 5. The product of the present invention can be used as a food ingredient. In one embodiment, the adduct is non-toxic. In one embodiment, the adduct can be hydrolysed to obtain non-toxic hydrolysis products.

The product may be a mixture, preferably having one or more constituents selected from the group consisting of: acesulfame, an acesulfame adduct and any other derivative of acesulfame. In one embodiment, the product comprises compounds with differing degrees of adduction. In one aspect of this embodiment, the product comprises acesulfame and one or more acesulfame adducts, the adducts preferably being with $SO_3$.

Test Methods

The following test methods are used for features disclosed in this document. In the absence of a test method, the ISO test method for the feature to be measured published most recently before the earliest filing date of the present application applies. In the absence of measuring conditions, a temperature of 298.15 K (25° C., 77° F.) and an absolute pressure of 100 kPa (14.504 psi, 0.986 atm) apply.

Detection of Chemical Species and Concentrations

Acesulfame content is determined by a combination of HPLC and UV spectroscopy according to the procedure described in "Monograph D acesulfame-K USP-NF" as published by "The United States Pharmacopeia and The National Formulary". The version of the monograph published most recently before the earliest filing or priority date of this document is employed.

Acetoacetamide-N-sulphonic acid salt content is calculated based on the contents of the input streams to the process.

$SO_3$ content is determined by distillation.

The content of solvents is determined by gas chromatography and Karl Fisher titration.

The yield of acesulfame is calculated based on the input content of sulphamic acid.

Reactor Temperature

The temperature in the reactor is calculated based on the reactor pressure according to the Antoine equation as follows:

$$\log_{10} p = A - B/(C+T)$$

in which p is the reactor pressure in bar ($10^5$ Pa), T is the reactor temperature in K and the three constants have the following values:

A=3.97323, B=1016.865, C=−56.623

Reactor Pressure & External Pressure

Pressure is measure using a piezo-resistive pressure transmitter Rosemount™ 3051 Coplanar™.

pH pH is measured using a Rosemount™ type 385 pH/ORP sensor.

Flow Rate

Flow rates are measured using a Rosemount™ type 8732 Magnetic Flowmeter System.

SUMMARY OF THE FIGURES

The invention is now further elucidated with reference to the figures. The figures and figure descriptions are exemplary and are not to be considered as limiting the scope of the invention.

The figures and descriptions focus on the features of the process relating to the invention and are not intended to be a comprehensive description of already established processes. The skilled person is aware of the technical details required to implement parts of the process which fall outside the focus of the invention, such as standard processes for distillation, phase separation and drying.

DESCRIPTION OF THE FIGURES

Figure 1:
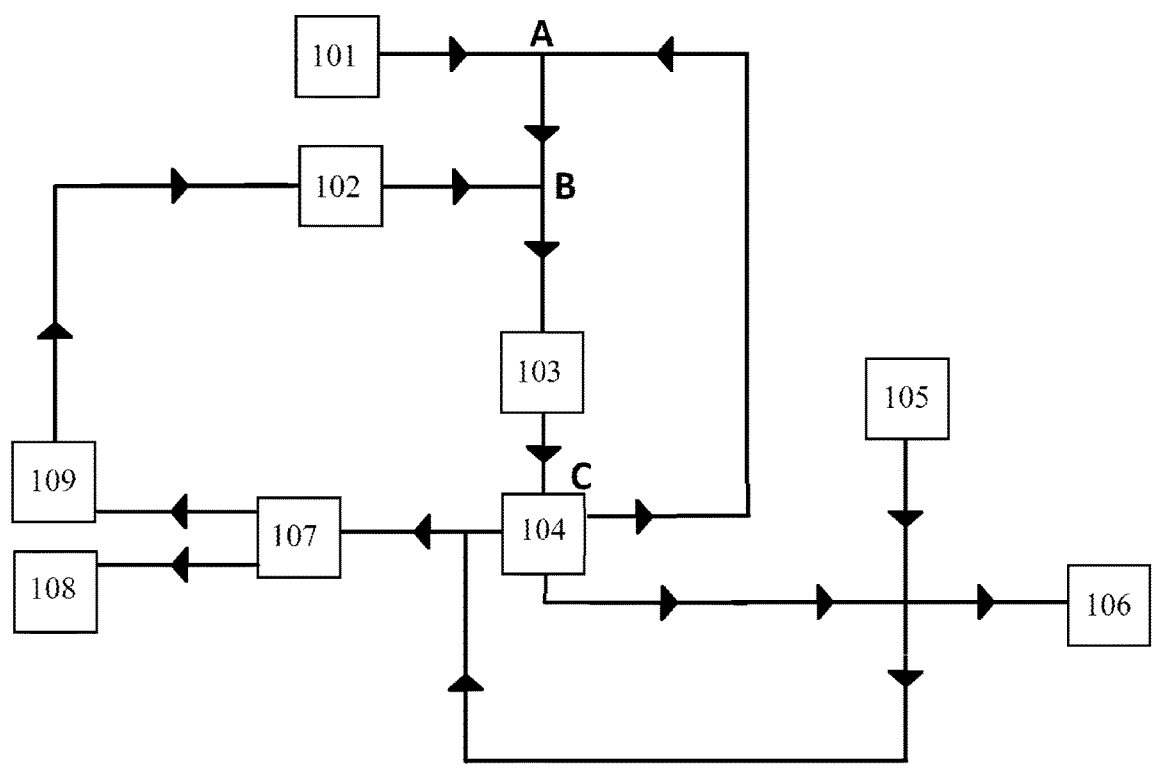
FIG. 1 is a schematic showing material flows in a process according to the invention.

FIG. 1 is a schematic showing material flows in a process according to the invention. A first stream 102 arising from a preparation process for acesulfame, comprising triethyl amine, sulphuric acid and water along with other trace constituents and a second stream 101 of liquid ammonia are introduced into a circuit to obtain a cycle stream, the first stream at point B and the second stream at point A in the circuit. The cycle stream is cooled or heated in a heat exchanger 103 and passed to a phase separator 104 at point C in the circuit. In the phase separator 104, a portion of the cycle stream called the third stream is separated into a liquid fifth stream comprising diammonium sulphate and $H_2O$ and a gaseous fourth stream comprising triethyl amine and $H_2O$. Part of the fifth stream is circulated into the cycle stream, in this case 8 to 15 times the flow of the first stream. The portion of the fifth stream leaving the circuit proceeds to be contacted with steam 105 to obtain aqueous diammonium sulphate solution which proceeds to further processing 106 and a steam portion which joins with the fourth stream. The further processing of the fifth stream comprises a solidification to obtain solid diammonium sulphate. The fourth stream along with the added steam component is distilled 107 into triethyl amine 108, which can be reused in the preparation of acesulfame, and a water fraction 109 which can be circulated back into the first stream 102.

Figure 2:
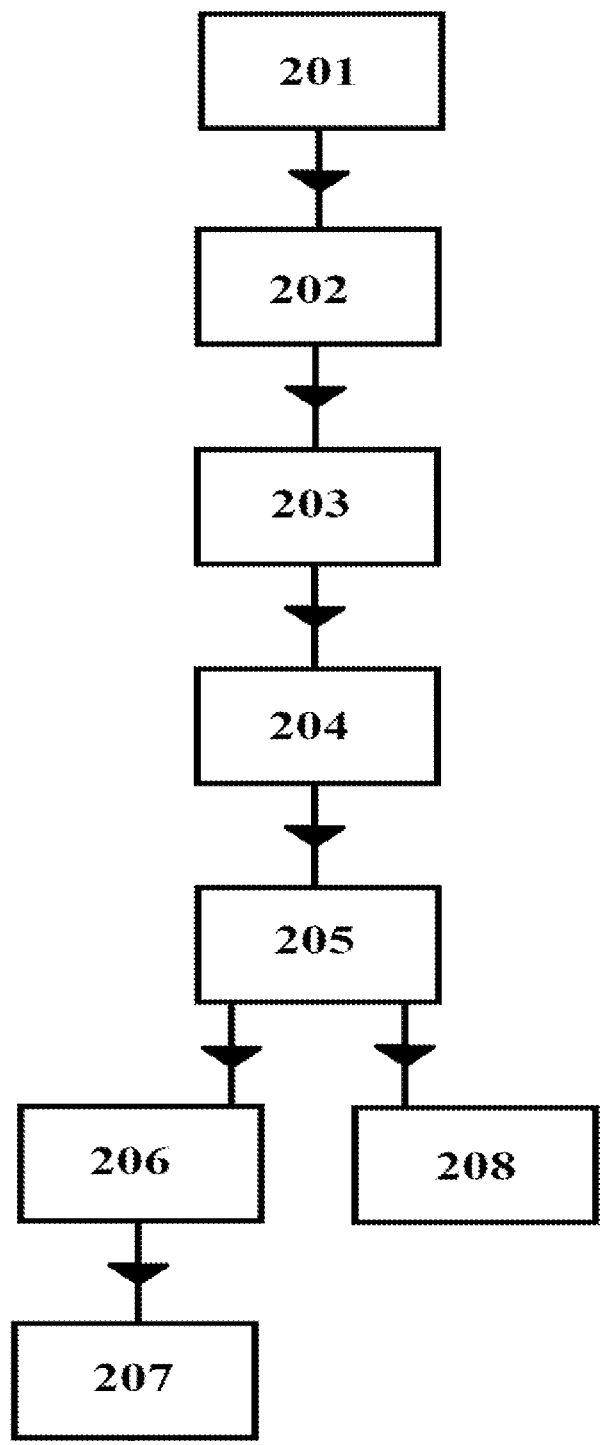
FIG. 2 is a schematic process flow showing the steps of the invention

FIG. 2 is a schematic process flow showing the steps of the invention. In a step a. 201 $SO_3$ and acetoacetamide-N-sulphonic acid are contacted to form an acesulfame. A first stream comprising $H_2O$, triethyl amine and sulphuric acid results from this step. In a step b. 202 a second stream of liquid ammonia is provided. In a step c. 203 a circuit is provided. In a step d. 204, the first and second streams are introduced into the circuit to obtain a cycle stream. In a step e. 205 a third stream is removed from the cycle. The third stream may be separated into a volatile fourth stream comprising triethyl amine and $H_2O$ and a liquid fifth stream comprising $H_2O$ and diammonium sulphate in a separation step f. The fifth stream may subsequently be contacted with $H_2O$ in the form of steam in step $g_1$ 206 and the resultant diammonium sulphate subsequently solidified in step $g_2$ 207. The fourth stream may be distilled in a step h. 208 to separate into a triethyl amine phase and a $H_2O$ phase. Purified triethyl-amine leaves the distillation at the column bottom.

Figure 3:
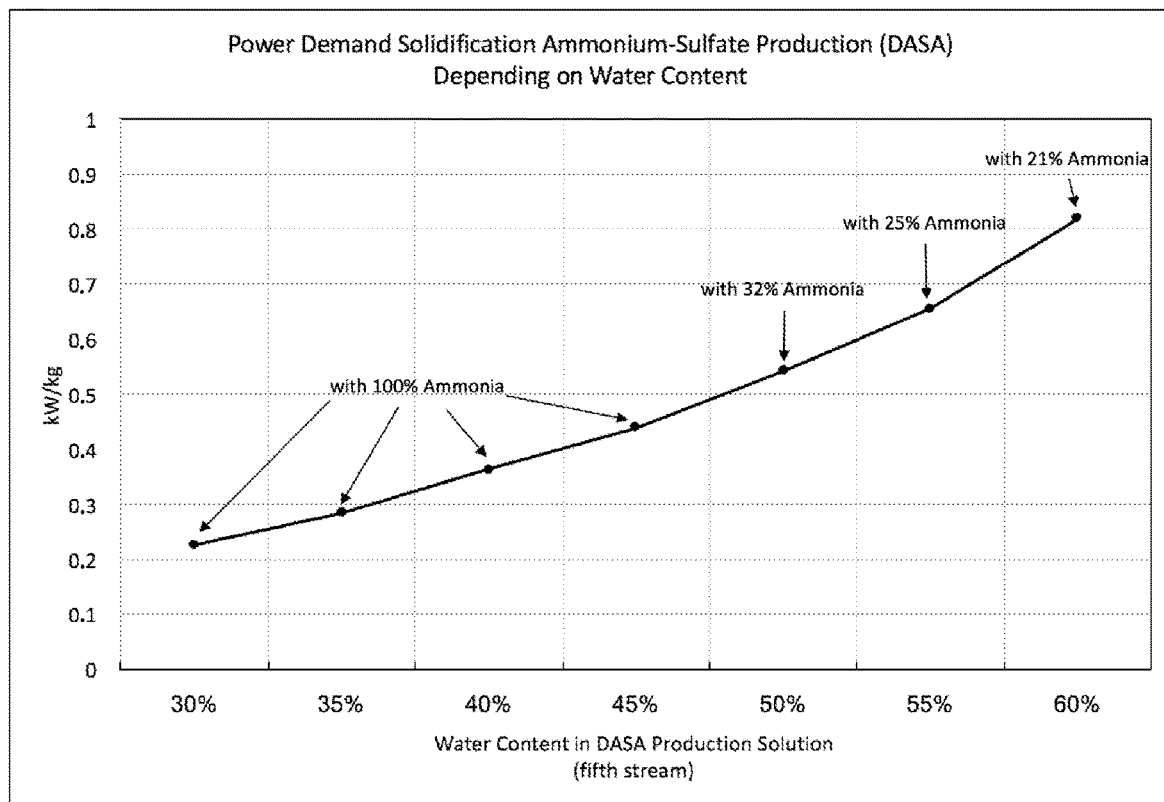
FIG. 3 is the graph showing the influence of water content in the production of diammonium sulphate on energy efficiency.
Figure 4:
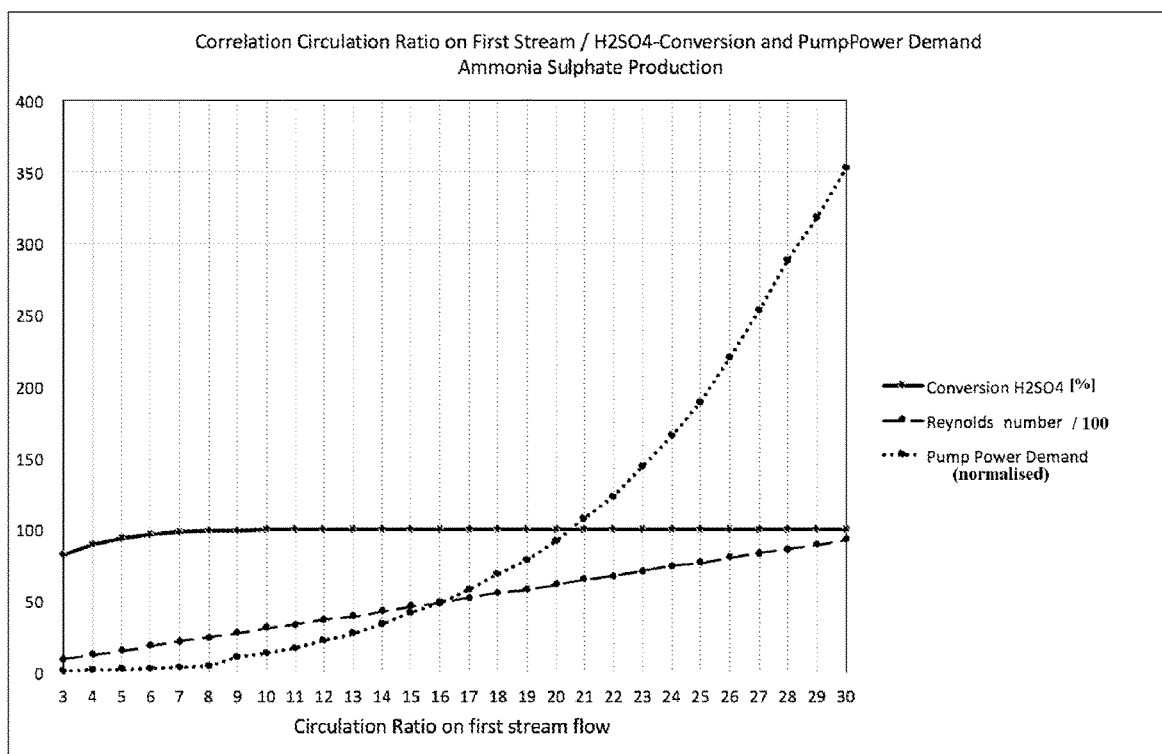
FIG. 4 is a graph showing the influence of circulation ratio on the conversion yield of sulphuric acid to diammonium sulphate as well as on pump parameters.

FIG. 3 further elucidates the influence of water content in the diammonium sulphate (DASA) solution (stream passing to solidification 106). The power requirements for drying are influenced by the water content. The power consumption was measured over the course of an hour FIG. 4 shows the effect of varying the circulation ratio on the proportional conversion of sulphuric acid into diammonium sulphate as well as the Reynolds number and energy consumption for the pump. The parameters were measured over the course of an hour.

EXAMPLES

The invention is now further elucidated with the aid of examples. These examples are for illustrative purposes and are not to be considered as limiting the scope of the invention.

General Procedure

A process was set up according to FIG. 1. The contacting step a. in which the acesulfame was created was performed as follows. The acetoacetamide-N-sulphonic acid supply was the triethylammonium salt of Acetoacetamide-N-sulphonic acid dissolved in dichloromethane (DKA) at a concentration of 1.5 molar. The $SO_3$ supply was $SO_3$ dissolved in dichloromethane (DCM/$SO_3$) at a concentration of 5 molar. The two supplies were provided to the reactor with volume flow ratio DKA:DCM/$SO_3$ of 1:1.2. A hydrolysis bed was provided with a flow of $H_2O$ which was adjusted such that the ratio of sulphuric acid:$H_2O$ by weight in the hydrolysis products was maintained in the range from 3:1 to 1:1. The sulphuric acid and triethyl amine products of the contacting and hydrolysis reaction were extracted using excess dichloromethane resulting in the first stream comprising 43 to 55 wt. % sulphuric acid and 10 to 12 wt. % triethyl amine in aqua. Pure liquefied ammonia or ammonia solutions were employed as the second stream. 10 times the input of the first stream was circulated to the cycle stream.

Examples 1 to 7

In Examples 1 to 4 the quantity of $H_2O$ was varied in the hydrolysis step yielding the concentrations in the first stream shown in table 1. The concentration of ammonia in the second stream in these examples was 100 wt. % (liquid ammonia). In examples 5 to 7 the first stream was the same as in example 1. Here the ammonia concentration in the second stream was varied, firstly taking the maximum soluble content in water at 20° C. of 36 wt. % (example 5), secondly taking a commercially employed value of 25 wt. % (example 6) and thirdly taking the value 21 wt. % (example 7).

TABLE 1

| | Contents of first stream [wt. %] | | | | Content of second stream [wt. %] |
|---|---|---|---|---|---|
| Example | $H_2SO_4$ | $H_2O$ | TEA | AcOH*TEA | $NH_3$ |
| 1 | 55 | 30 | 12 | 3 | 100 |
| 2 | 51 | 35 | 11 | 3 | 100 |
| 3 | 47 | 40 | 11 | 2 | 100 |
| 4 | 43 | 45 | 10 | 2 | 100 |
| 5 | 55 | 30 | 12 | 3 | 32 |
| 6 | 55 | 30 | 12 | 3 | 25 |
| 7 | 55 | 30 | 12 | 3 | 21 |

Results for the power requirement for spray drying of the diammonium sulphate are shown in table 2 and presented in FIG. 3. The power consumption was measured over the course of an hour.

TABLE 2

Energy Efficiency

| Example | $H_2O$ content in DASA production [wt. %] | Spray drying kW/kg DASA |
|---|---|---|
| 1 | 30 | 0.226 |
| 2 | 35 | 0.284 |
| 3 | 40 | 0.363 |
| 4 | 45 | 0.439 |
| 5 | 50 | 0.542 |
| 6 | 55 | 0.655 |
| 7 | 60 | 0.82 |

Example 8

The procedure was repeated according to example 1, except that the circulation ratio was varied as per table 3. The proportion of sulphuric acid converted, the Reynolds number and the pump power demand are also displayed in table 3. Results are displayed in FIG. 4. The parameters were measured over the course of an hour.

TABLE 3

| Example | Circulation ratio | Conversion of sulphuric acid [%] | Reynolds number | Pump power demand (Normalised) |
|---|---|---|---|---|
| 8a | 3 | 82 | 930 | 1 |
| 8b | 4 | 89 | 1276 | 1.72 |
| 8c | 5 | 94 | 1508 | 2.47 |
| 8d | 6 | 96.5 | 1856 | 3.22 |
| 8e | 7 | 98 | 2204 | 4.17 |
| 8f | 8 | 99 | 2436 | 4.89 |
| 8g | 9 | 99.5 | 2784 | 11.34 |
| 8h | 10 | 99.7 | 3132 | 14.03 |
| 8i | 11 | 99.7 | 3364 | 17.52 |
| 8j | 12 | 99.7 | 3712 | 22.75 |
| 8k | 13 | 99.7 | 3944 | 27.44 |
| 8l | 14 | 99.7 | 4292 | 34.11 |
| 8m | 15 | 99.7 | 4640 | 41.94 |
| 8n | 16 | 99.7 | 4872 | 48.8 |
| 8o | 17 | 99.7 | 5220 | 57.94 |
| 8p | 18 | 99.7 | 5568 | 69.2 |
| 8q | 19 | 99.7 | 5800 | 78.56 |
| 8r | 20 | 99.7 | 6148 | 91.63 |
| 8s | 21 | 99.7 | 6496 | 108.47 |
| 8t | 22 | 99.7 | 6728 | 123.31 |
| 8u | 23 | 99.7 | 7076 | 144.3 |
| 8v | 24 | 99.7 | 7424 | 165.89 |
| 8w | 25 | 99.7 | 7656 | 188.75 |
| 8x | 26 | 99.7 | 8004 | 220.61 |
| 8y | 27 | 99.7 | 8325 | 253.63 |
| 8z | 28 | 99.7 | 8584 | 287.63 |
| 8aa | 29 | 99.7 | 8923 | 318.7 |
| 8bb | 30 | 99.7 | 9280 | 352.78 |

REFERENCE LIST

101 Second stream
102 First stream
103 Cooler
104 Phase separator
105 Steam
106 Crystallisation
107 Distillation
108 Triethyl amine phase
109 $H_2O$ phase
201 Step a.
202 Step b.
203 Step c.
204 Step d.
205 Step e
206 Step $g_1$
207 Step $g_2$
208 Step h

The invention claimed is:

1. A process for the preparation of a product, the product being 6-methyl-3,4-dihydro1,2,3-oxathiazin-4-one 2,2-dioxide or a salt thereof, the process comprising the following steps:
   a. Contacting $SO_3$ and acetoacetamide-N-sulphonic acid or a salt thereof, in the presence of an amine, thereby obtaining a first stream comprising the amine and sulphuric acid;
   b. Providing a second stream comprising ammonia;
   c. Providing a circuit;
   d. Introducing the second stream into the circuit at point A and the first stream into the circuit at point B to obtain a cycle stream cycling in the circuit;
   e. Removing a portion of the cycle stream at a point C to obtain a third stream;
   wherein the circulation ratio is in the range from 3 to 30, the circulation ratio being the value of the mass flow rate of the cycle stream immediately preceding point A $F_c$ divided by the value of the mass flow rate of the first stream into the circuit at point B $F_1$ according to the following formula:

$$\text{circulation ratio} = F_c/F_1.$$

2. The process according to claim 1, wherein the amine is triethyl amine.

3. The process according to claim 1, wherein the third stream is removed from the cycle stream at a point C and the points A, B & C are ordered in the direction of the flow of the cycle stream in the circuit.

4. The process according to claim 1, wherein the second stream does not comprise more than 50 wt. % $H_2O$.

5. The process according to claim 1, wherein the second stream is a liquid.

6. The process according to claim 1, wherein the second stream is at a pressure in the range from 0.2 to 1.5 MPa.

7. The process according to claim 1, further comprising the following step:
   f. Separating the third stream to obtain a fourth stream comprising the amine and a fifth stream comprising diammonium sulphate;
   wherein the fourth stream comprises a higher wt. % of the amine than the first stream;
   wherein the fourth stream comprises a lower wt. % of diammonium sulphate than the first stream.

8. The process according to claim 7, wherein the fifth stream is contacted with $H_2O$ in a step $g_1$.

9. The process according to claim 8, wherein least part of the $H_2O$ is present in step $g_1$ in a gaseous state.

10. The process according to claim 7, wherein the mass ratio of the fourth stream to the fifth stream is in the range from 30:70 to 1:99.

11. The process according to claim 7, wherein the content of $H_2O$ in the fifth stream is reduced in a step $g_2$.

12. The process according to claim 11, wherein the step $g_2$ is a solidification.

13. The process according to claim 7, wherein the fourth stream is separated into a sixth stream and a seventh stream in a step h;
   wherein the seventh stream comprises more $H_2O$ than the sixth stream;

wherein the sixth stream comprises more of the amine than the seventh stream.

14. The process according to claim 13, wherein the step h is a distillation.

15. The process according to claim 1, wherein the cycle stream is heated or cooled.

* * * * *